(12) United States Patent
Kowal et al.

(10) Patent No.: US 9,907,466 B2
(45) Date of Patent: Mar. 6, 2018

(54) OPTICAL COHERENCE TOMOGRAPHY IMAGING DEVICE FOR IMAGING A RETINA OF A HUMAN SUBJECT

(71) Applicant: MIMO AG, Bern (CH)

(72) Inventors: Jens Kowal, Seftigen (CH); Peter Maloca, Lucerne (CH); Bruno Rieder, Naters (CH)

(73) Assignee: MIMO AG, Bern (CH)

( * ) Notice: Subject to any disclaimer, the term of this patent is extended or adjusted under 35 U.S.C. 154(b) by 0 days.

(21) Appl. No.: 15/309,552

(22) PCT Filed: Apr. 14, 2015

(86) PCT No.: PCT/CH2015/000056
§ 371 (c)(1),
(2) Date: Nov. 8, 2016

(87) PCT Pub. No.: WO2015/168812
PCT Pub. Date: Nov. 12, 2015

(65) Prior Publication Data
US 2017/0172407 A1 Jun. 22, 2017

(30) Foreign Application Priority Data
May 8, 2014 (CH) ........................................ 700/14

(51) Int. Cl.
*A61B 3/14* (2006.01)
*A61B 3/10* (2006.01)
(Continued)

(52) U.S. Cl.
CPC ............ *A61B 3/102* (2013.01); *A61B 3/0075* (2013.01); *A61B 3/0083* (2013.01);
(Continued)

(58) Field of Classification Search
USPC .................................................. 351/200–246
See application file for complete search history.

(56) References Cited

U.S. PATENT DOCUMENTS

| | | |
|---|---|---|
| 5,033,840 A | 7/1991 | Hennequin et al. |
| 5,943,116 A | 8/1999 | Zeimer |

(Continued)

FOREIGN PATENT DOCUMENTS

| | | |
|---|---|---|
| EP | 1 321 095 A2 | 6/2003 |
| EP | 1 882 444 A1 | 1/2008 |

(Continued)

*Primary Examiner* — Mohammed Hasan
(74) *Attorney, Agent, or Firm* — Birch Stewart Kolasch & Birch, LLP (57) ABSTRACT

An optical coherence tomography imaging device (1) for imaging a retina of a human subject comprises a base (10) having a planar contact surface (11), an optical unit (30) providing a sample beam to scan the retina of the human subject and a head support (80) to be contacted by a head portion of the human subject, the head support (80) defining an entrance position of the sample beam entering an eye of the human subject. An angle between the sample beam at the entrance position and the planar contact surface (11) of the base (10) is 50 to 90°. This arrangement ensures that the head rests in a stable and well defined position with respect to the OCT optics. The risk of negative effects on the imaging process due to head movements, in particular due to movements during the scan time of the OCT device is considerably reduced. Furthermore, the device may assume a compact form factor.

17 Claims, 5 Drawing Sheets

(51) Int. Cl.
*A61B 3/12* (2006.01)
*A61B 3/00* (2006.01)
*G02B 27/00* (2006.01)
*G02B 27/30* (2006.01)

(52) U.S. Cl.
CPC .............. *A61B 3/1225* (2013.01); *A61B 3/14* (2013.01); *G02B 27/0068* (2013.01); *G02B 27/30* (2013.01)

(56) References Cited

U.S. PATENT DOCUMENTS

| | | | |
|---|---|---|---|
| 7,792,249 B2* | 9/2010 | Gertner | A61F 9/008 378/65 |
| 8,237,835 B1* | 8/2012 | Muller | A61B 3/1025 250/201.9 |
| 9,730,580 B2* | 8/2017 | Verdooner | A61B 3/102 |
| 2002/0047995 A1 | 4/2002 | Walther | |
| 2004/0032568 A1 | 2/2004 | Fukuma et al. | |
| 2009/0180074 A1 | 7/2009 | Benyamini et al. | |
| 2016/0022134 A1* | 1/2016 | Ryan | A61B 3/0083 351/206 |

FOREIGN PATENT DOCUMENTS

| | | |
|---|---|---|
| WO | WO 2008/150330 A1 | 12/2008 |
| WO | WO 2009/120543 A1 | 10/2009 |
| WO | WO 2010/060622 A1 | 6/2010 |

* cited by examiner

OPTICAL COHERENCE TOMOGRAPHY IMAGING DEVICE FOR IMAGING A RETINA OF A HUMAN SUBJECT

TECHNICAL FIELD

The invention relates to an optical coherence tomography imaging device for imaging a retina of a human subject, comprising a base having a planar contact surface, an optical unit providing a sample beam to scan the retina of the human subject and a head support to be contacted by a head portion of the human subject, the head support defining an entrance position of the sample beam entering an eye of the human subject.

BACKGROUND ART

Age-related Macular Degeneration (AMD) and especially neovascular AMD (nAMD) is the leading cause of blindness in the developed countries in people ageing over 50 years. An increase in vascular permeability leads to abnormal fluid collection within or below the retina that causes visual dysfunction when it involves the center of the macula. This leads to rapidly deteriorating acuity, scarring of the pigment epithelium, and permanent visual loss or blindness.

However, intravitreal injection of antiangiogenic agents, including Ranibizumab (trade name Lucentis®, Novartis, Basel, Switzerland), has been shown to significantly improve the course of nAMD. To reduce the burden of intravitreal injections and to optimize the risk/benefit profile, the progression of nAMD features can be monitored non-invasively by Optical Coherence Tomography (OCT). Prominent nAMD features involve the increase of the thickness of retinal structures. Such an increase may be identified when visually comparing two OCT images of the same region of the retina taken at different times, the temporal distance being several days to several months.

For instance, patients treated with Ranibizumab usually undergo an OCT examination every month. If a significant growth in nAMD features is observed, then a treatment decision is indicated: the patient receives a Ranibizumab injection that day, one month later and two months later (treatment phase). Retreatment can be indicated one month later if the nAMD features have not completely receded. Otherwise, the patient does not receive an injection that day, but regularly indicated maintenance injections (maintenance phase).

For the OCT acquisition usually sophisticated and correspondingly expensive state-of-the-art OCT devices are employed. They are located at medical offices or specialized units of hospitals. The devices are operated by skilled personnel. This means that the monitored patients are required to visit a medical office or specialized unit of a hospital each time an OCT has to be acquired. This puts a considerable burden upon the patients. Furthermore, the frequency of the OCT acquisitions (such as 1 month) is already sort of a compromise between on one hand close monitoring of the development of nAMD and on the other hand the costs and the burden on the patient.

These problems may be alleviated if OCT image acquisition devices are located closer to the patients, in particular if the monitored patients have access to an OCT imaging device at their home. This is only feasible if the OCT devices are compact, comparably inexpensive and may be operated by essentially anyone, most preferably by the patient himself or herself. However, today such devices are not available.

SUMMARY OF THE INVENTION

It is the object of the invention to create an OCT imaging device pertaining to the technical field initially mentioned, that is inexpensive, compact and easy to use.

The solution of the invention is specified by the features of claim 1. According to the invention an angle between the sample beam at the entrance position and the planar contact surface of the base is 50 to 90°. In particular the angle is 60 to 90°, notably the angle is 75 to 85°.

Today's OCT devices usually require the patient to be in a sitting position, holding his or her head straight, the optical axes of the eyes essentially having a horizontal orientation. Accordingly, at the entrance position, the sample beam is also essentially horizontal. If the OCT device has a base with a planar contact surface, e.g. positioned on a tray, the sample beam therefore is essentially parallel to the contact surface.

It has turned out that the inventive orientation of the beam, having an angle of 50 to 90°, in particular 60 to 90°, preferably 75 to 85°, relative to the planar contact surface, i.e. relative to a horizontal plane, ensures that the head rests in a stable and well defined position with respect to the OCT optics. The risk of negative effects on the imaging process due to head movements, in particular due to movements during the scan time of the OCT device is considerably reduced. This is due to the fact that a considerable part of the head's weight is rested on the head support and thus stabilizes the head position. Furthermore, in this position, the patient has no tenseness in the neck and is relaxed. This results to no or at most very small movements of the head and allows taking OCT-Pictures of the retina without artefacts.

Furthermore, the inventive configuration allows for reducing the size of the device. In particular, it is preferred that the device has a tabletop configuration, i.e. that the entering position has an ergonomic position for a sitting patient if the planar contact surface (being the lower outer surface of the device) contacts a tabletop, which is the case if a distance between the contact surface of the base and the entrance position is 20 to 50 cm. Compared to a device requiring the horizontal orientation of the eyes' optical axes the height of the device may be reduced by about 15 cm, which is about one third of the total height of the tabletop device. Correspondingly, the device is easier to carry and to stow away and its weight may be reduced.

The optical unit will contain beam forming and directing optics, in particular a scanning unit. It may further comprise a light source, a detector, means for tracking the position of the examined eye and further elements required for the OCT process. A spectrometer may be part of the optical unit or arranged remotely, e.g. on the base.

Preferably the head support comprises a support portion for accommodating an eye portion of the head of the human subject. The support portion thus comprises support surfaces that may be contacted by facial regions surround one or both eyes of the human subject. This ensures that the eye position is as stable as possible and thus negative effects on the imaging process due to head movement are avoided. The support portion may be mask like and essentially match the shape of the eye area of the face.

Preferably, the eye portion encloses both eyes of the human subject and the optical unit is designed to inspect both eyes of the human subject without having to change the head's position with respect to the head support. For that purpose, the position of the optical unit may with respect to the base be adjustable, the optical unit comprises optical elements that allow for reaching both eyes, or the optical unit comprises separate optics for the two eyes.

Alternatively or in addition, the head support comprises one or several support portions that contact other areas of the head such as the forehead, the chin, etc.

Preferably, the head support comprises a nose bone clip to contact a nose bone of the human subject. The nose bone clip contacts both sides of the nose bone and therefore clearly defines the head's position with respect to the head support. Preferably, the nose bone clip includes two legs, each of those contacting one side of the nose bone. In connection with the support in the eye area, the nose bone clip ensures a stable and reproducible positioning of the subject's head.

Advantageously, the nose bone clip is adjustable in a longitudinal direction. In this context, "longitudinal" refers to a direction that is essentially parallel to the bridge of the nose and lies in the sagittal plane of the subject's head. Longitudinal adjustment allows for adjusting the head support to the subject's head in an optimum way.

Similarly, it is preferred that an orientation of the nose bone clip about a lateral axis is adjustable. Lateral is a direction perpendicular to the aforementioned longitudinal direction and perpendicular to the sagittal plane of the head of the subject. Again, this adjustability improves the adaptation of the head support to the head and therefore ensures accurate positioning of the head with respect to the OCT device.

In a preferred embodiment, the head support comprises an insert that is made to fit a specific anatomy of the head of the human subject. This may be achieved in several ways, e.g.:
a) the insert may be manufactured based on an imprint of the supported portion of the human subject's head, e.g. by casting techniques or CNC machining;
b) the insert may be manufactured based on a three-dimensional image of the supported portion of the human subject's head, in particular by CNC machining;
c) the insert may be made from a ductile material, which essentially maintains its form once it has been deformed.

Alternatively, the head support does not comprise such an insert but is available in a certain number of standard sizes and may be adapted to the head by means of the adjustable nose bone clip and/or further adjustable elements.

In a preferred embodiment, the head support is attached to the base in a fixed longitudinal and lateral position, whereas the optical unit is movable with respect to the base in such a way that entrance positions differing in at least a lateral direction are reachable by the sample beam. Thus, the head support is solidly mounted and both eyes of the human subject may be captured by a single optical arrangement. The unit may be moved manually, but it is preferred to have a drive motor that allows for precisely positioning the optical unit in the at least lateral direction. In addition to the choice of the eye to be examined, the degrees of freedom of the optical unit allow for fine tuning of the adjustment of the optical device with respect to the eye to be examined. The optical unit may be movable along a linear axis or along linear axes, in particular axes parallel to the planar contact surface of the base. In other embodiments, the optical unit may be pivotable about a pivot axis or about pivot axes. Linear axes and pivot axes may be combined.

The head support may be attached to a housing which encloses the optical unit. Alternatively, a frame carrying the head support is attached to the base.

Despite the attachment in a fixed position, it is preferred that an orientation of the head support about a horizontal lateral axis is adjustable. This allows for modifying the angle of the subject's head with respect to the device and therefore ensures an ergonomic and comfortable positioning for the OCT measurement. Again, it is preferred to have a drive motor to effect the adjustment.

Preferably, a height of the optical unit with respect to the base is adjustable. Again, this allows for precisely adjusting the positioning of the optical elements of the optical unit with respect to the eye to be examined.

As an alternative or in addition, a height of the head support with respect to the base is adjustable. Besides optical adjustment, this also allows for further improving the ergonomy of the device. In a simplified embodiment, the base features height-adjustable feet such that the height of the entire device is adjustable.

In a preferred embodiment, the optical unit comprises an adjustable collimator lens for adapting the sample beam to an ametropia of the examined eye of the human subject. Compared to prior art solutions where usually the telescope lens system is adjusted, this leads to a more compact arrangement taking into account the spatial circumstances in compact OCT devices. Adjusting the collimator lens leads to a slightly convergent or divergent beam and is therefore a suitable and simple means of adaptation to conditions such as myopia or hyperopia.

The use of an adjustable collimator lens is not restricted to OCT devices having an angle between the sample beam at the entrance position and the planar contact surface of the base of 50 to 90°, but may also be employed in connection with other OCT devices.

In a first embodiment, a shape of the collimator lens is adjustable. Corresponding lenses are available on the market, e.g. variable focus liquid lenses.

In a second embodiment, the position of the collimator lens along a beam axis is adjustable. Adjusting this position will lead to "not enough" or "too much" collimation of the incoming beam and therefore to the desired result of having a slightly convergent or divergent beam. Adjusting may be effected by a screw that is accessible from the outside, or a linear drive or a voice coil system may be used for moving the collimator lens.

Most preferred, the collimator lens is arranged following an output of an optical fiber, whereas the distance between the collimator lens and the output is adjustable. This is a reliable, space-saving and cost-effective arrangement.

Other advantageous embodiments and combinations of features come out from the detailed description below and the totality of the claims.

BRIEF DESCRIPTION OF THE DRAWINGS

The drawings used to explain the embodiments show.

In the figures, the same components are given the same reference symbols.

PREFERRED EMBODIMENTS

Figure 1:
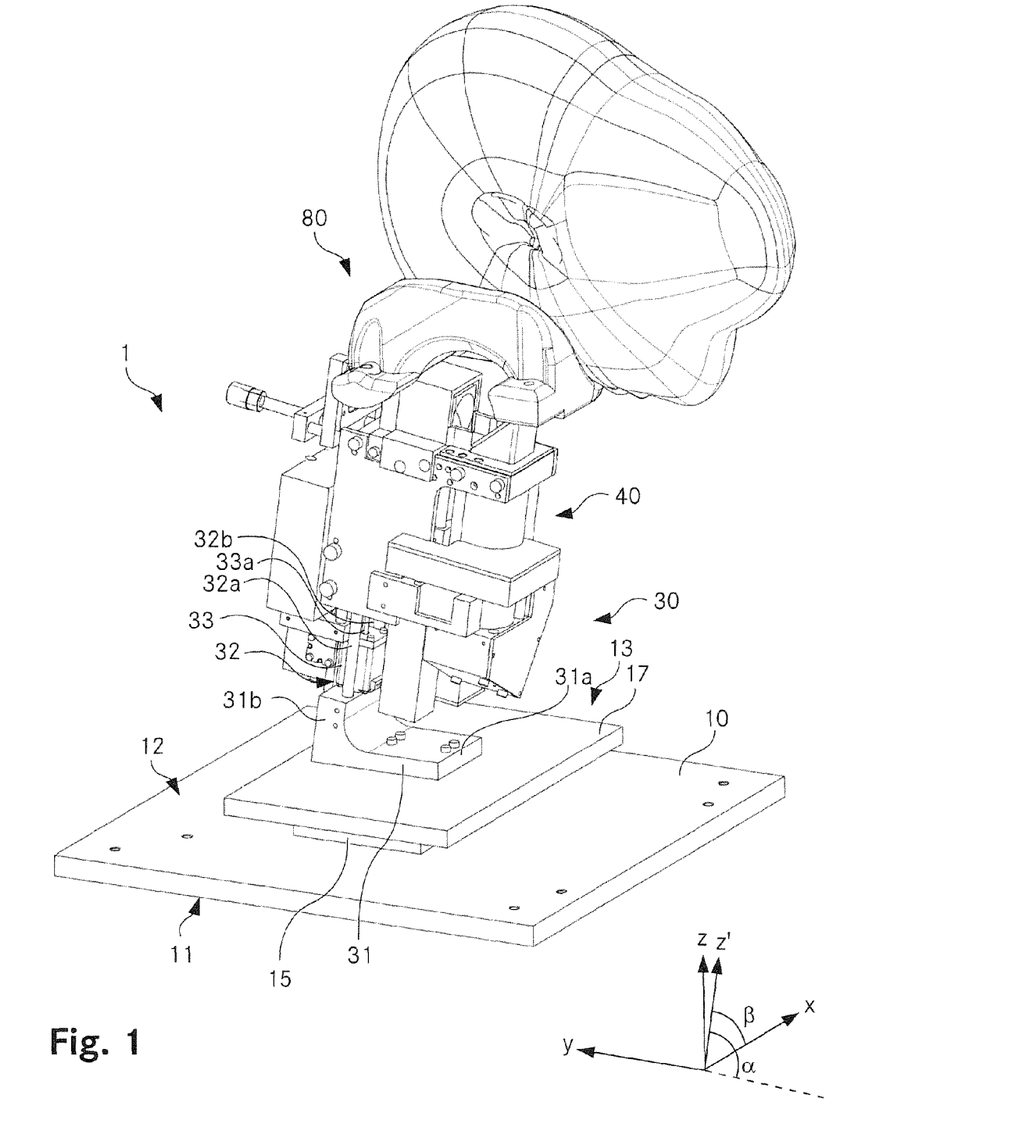
FIG. 1 An articulated view of an OCT device according to an embodiment of the invention.
Figures 2, 3:
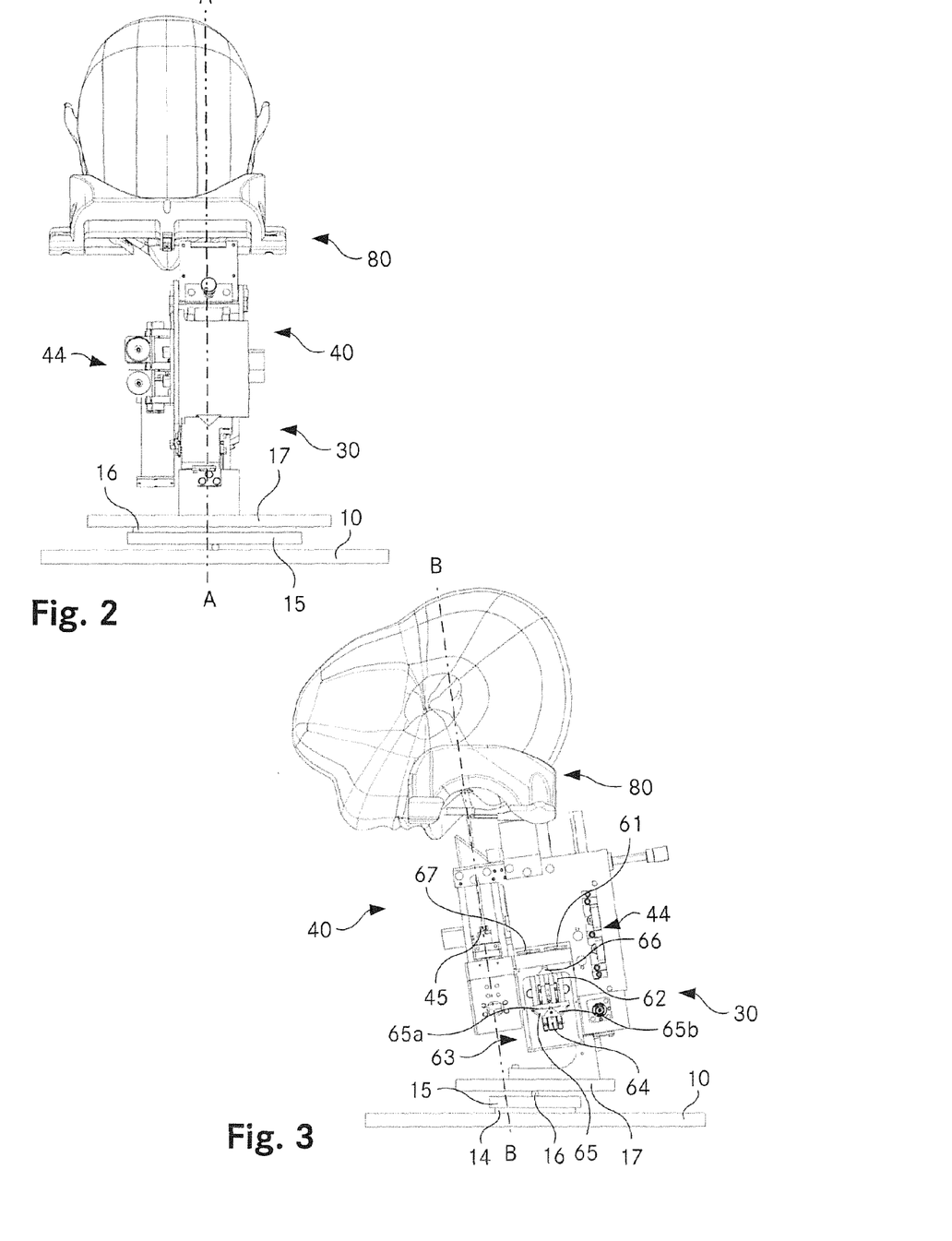
FIG. 2 a frontal view of the OCT device.
FIG. 3 a side view of the OCT device.
Figures 4, 5:
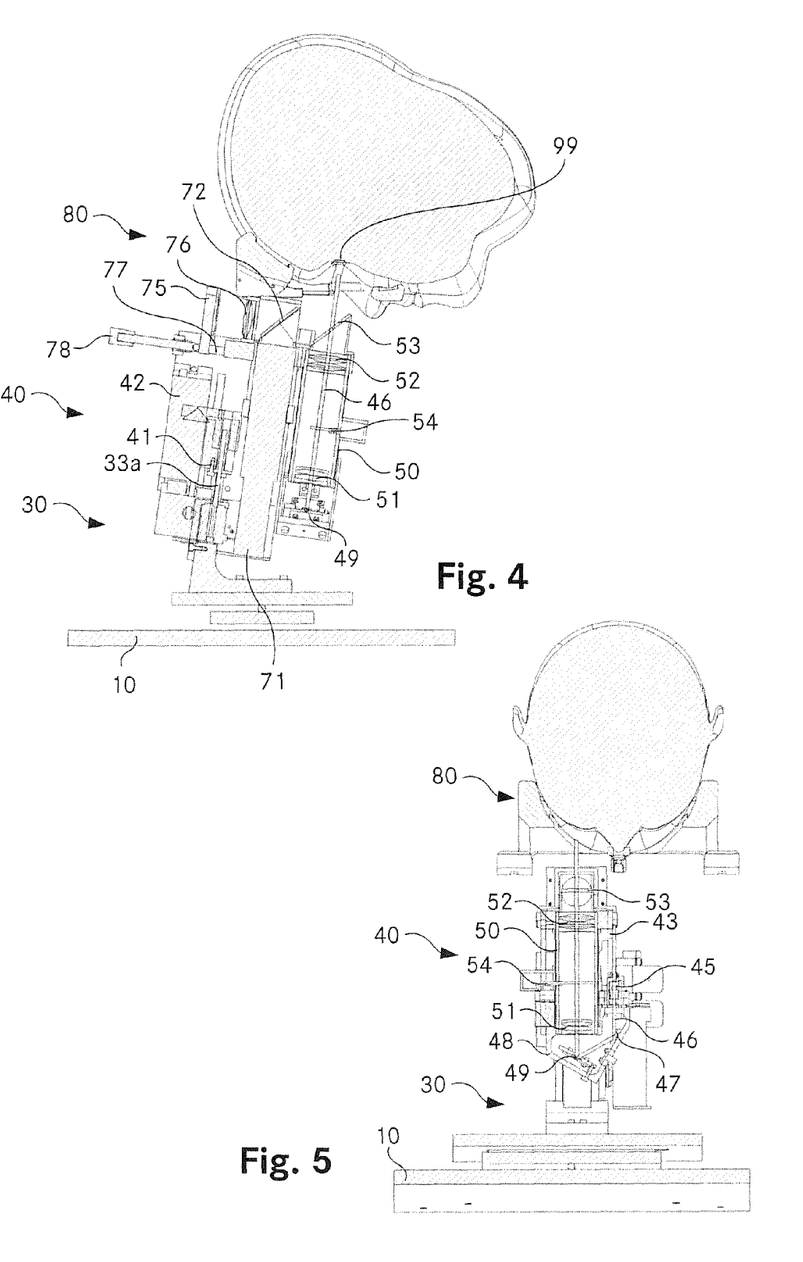
FIG. 4 a cross-sectional view of the OCT device in an yz plane.
FIG. 5 a cross-sectional view of the OCT device in an xz' plane.

FIG. 1 shows an articulated view of an OCT device according to an embodiment of the invention. FIG. 2 shows a frontal view, FIG. 3 a side view of the OCT device, as seen from the right hand side. FIGS. 4 and 5 show cross-sectional views of the OCT device, FIG. 4 in a yz plane A-A shown in FIG. 2, FIG. 5 in the xz' plane B-B shown in FIG. 3, seen from behind. For simplicity and in order to provide an overview, a housing surrounding the main optical unit as well as a spectrometer have been omitted in the Figures.

The main components of the OCT device 1 are a base plate 10, an optical unit 30 movable mounted to an upper surface of the base plate 10 and a head support 80 arranged above the optical unit 30.

The base plate 10 is rectangular and has uniform thickness. Its size is about 40×40 cm. The base plate 10 comprises a lower surface 11, which is a support surface for the OCT device 1 to be put on a flat surface such as a tabletop, and an upper surface 12 to which the optical unit 30 and the head support 80 are mounted. In the Figures, the mounting of the head support 80 is not shown. However, in principle, the head support 80 may be attached to the upper end of a housing surrounding the optical unit 30.

On the upper surface 12 of the base plate 10 a pivoting mechanism 13 supporting a foot 31 of the optical unit 30 is mounted. The pivoting mechanism 13 allows for pivoting the optical unit 30 about two horizontal pivot axes, the axis running along the x and the y direction, both being parallel to the lower and the upper surface 11, 12 of the base plate 10. As can be seen from FIGS. 1-3, the pivoting mechanism 13 comprises a lower pivot axis 14, running in y direction, allowing for adjusting an angle β between the z' axis of the optical unit 30, which corresponds to the direction of the sample beam emitted by the optical unit 30, and the x axis. The lower pivot axis 14 is arranged between the upper surface 12 of the base plate 10 and a lower support plate 15. An upper pivot axis 16, running in x direction, i.e. perpendicular to the lower pivot axis 14, is arranged between the lower support plate 15 and an upper support plate 17. It allows for adjusting the angle α between the z' axis of the optical unit 30 and the y axis. The foot 31 of the optical unit 30 is fixedly attached to the upper support plate 17.

Both pivot axes 14, 16 comprise shafts that are rotatable about their longitudinal axes and which link the two neighbouring elements. The pivoting angle is set by step motors counteracting springs.

The foot 31 of the optical unit 30 is essentially L-shaped, having a first leg 31a extending parallel to the base plate 10 and a second leg 31b connected to the first leg 31a, the first leg 31a and the second leg 31b enclosing an angle α of approximately 82°, depending on the position of the upper pivot axis 16, defining an angle of the axis of the measurement beam with respect to the base 10, as described below. A linear guide 32 is attached to the upper end of the second leg 31b. The linear guide 32 comprises two threaded bars 32a, 32b extending parallel to the second leg 31b and coupled to it in a rotationally fixed manner. The threaded bars 32a, 32b cooperate with threaded nuts rotatably mounted to the upper part 40 of the optical unit 30. A motor 33 is attached to the upper surface of the second leg 31b driving a threaded spindle 33a. This threaded spindle 33a cooperates with a threaded nut 41 fixedly attached to the upper part 40 of the optical unit 30 (see FIG. 4). Using the motor 33 attached to the foot 31, the position of the upper part 40 of the optical unit 30 relative to the z' axis may be adjusted.

The upper part 40 of the optical unit 30 houses the main optical elements of the OCT device 1. The laser light source 42 generating a beam having a wavelength of about 835 nm or higher is housed in a front region of the upper part 40, ahead of the threaded nut 41 and the guide channel for the threaded spindle 33a driven by motor 33 for the z' movement. To the output of the laser light source 42 an optical fiber is connected. The fiber leads to an optical coupler (not shown) where the incoming light beam is split into a measurement beam and a reference beam. The optical coupler may be arranged at the right side of the upper part 40 of the optical unit 30. The measurement beam is coupled into a further optical fiber 43. A section of the latter is coiled up and housed in a coil housing 44 attached to a side wall of the upper part 40, the coil axis lying in the yz plane and being perpendicular to the z' axis. This arrangement allows for controlling the polarization of the measurement beam. The output of the optical fiber 43 is coupled into a collimator 45 comprising a collimator lens. In the shown embodiment, the collimator lens is adapted to monochromatic light and has a focal length of 5.1 mm. A distance between the end of the optical fiber 43 and the collimator lens is adjustable. This allows for adjusting the collimation, in particular the collimation may be chosen to be slightly overdone or slightly incomplete in order to easily compensate hyperopia or myopia of the examined eye, respectively.

The collimated light beam 46 is reflected by a mirror 47 arranged in a first leg of a V-shaped element 48 of the upper part 40 of the optical unit 30. Next, it impinges on a 4-quadrant MEMS mirror 49 in a second leg of the V-shaped element 48. The MEMS mirror 49 has a scanning angle of ±5° and allows for adjusting the direction of the light beam 46 in the x and y directions. Next, the light beam 46 passes a telescope 50 including two lens packages 51, 52 including two lenses each, for projecting the light beam 46 to a pupil of an eye 99 to be examined. In the shown embodiment, all lenses have a diameter of 30 mm, their effective focal length is 100 mm (first lens of the first lens package 51 as well as both lenses of the second lens package 52) and 200 mm, respectively (second lens of the first lens package 51). After passing a dichroic mirror 53 (longpass, 760 nm) the focused light beam 46 enters the eye 99 at an entrance position.

In the described example, the distance between the center of the MEMS mirror 49 and the first lens of the first lens package 51 is 23 mm, the distance between lens packages 51, 52 is 75 mm, the distance between the second lens package 52 and the dichroic mirror 53 is approximately 25 mm, the distance between the center of the dichroic mirror 53 and the entrance position is approximately 43 mm. A plate-shaped blocking element 54 made from aluminium is movably mounted in the region of the telescope 50 and may be inserted by means of actuating an associated drive to block the optical path as well as retracted by the same drive to free the optical path. Blocking the path allows for taking reference measurements for calibration purposes.

Backscattered light of the focused light beam 46 travels back the same optical path, i.e. passes the dichroic mirror 53, is reflected by the MEMS mirror 49 and the mirror 47, is coupled back into the optical fiber 43 and led back to the optical coupler.

At the aforementioned optical coupler, the reference beam is coupled to a further optical fiber which leads to a further collimator 61. The collimated reference beam 62 enters an adjustable reference arm unit 63 arranged at the right side of the upper part 40 of the optical unit 30. The reference arm unit 63 comprises a linear guide 64, running parallel to the reference beam 62, on which a carriage 65 is guided, its position along the guide 64 being precisely adjustable by means of a linear motor. Attached to the carriage 65 are two prisms 65a, 65b for deflecting incoming light by 180°. A third prism 66 is fixedly attached to the reference arm unit 63. Finally, a mirror 67 is also fixedly attached to the reference arm unit 63. The three prisms 65a, 65b, 66 and the mirror 67 are arranged in such a way that the incoming reference beam 62 is deflected by the first prism 65a of the carriage 65, by the third prism 66 fixedly attached to the reference arm unit 63 and by the second prism 65b of the carriage 65, is subsequently reflected by the mirror 67 and returns on the same optical path. Finally, the reflected reference beam is coupled back into the respective optical fiber and led back to the optical coupler. The total path length of the reference beam may be adjusted by adjusting the position of the carriage 65 with respect to the linear guide 64. This allows for compensating for the back and forward movement of the head and tolerances of the headrest. In particular, the required path length in the reference arm may be about 230 mm, where the adjustment range is approximately 185-280 mm.

In the optical coupler, the reflected reference beam and the backscattered light of the measurement beam are recombined and coupled into a further optical fiber. This fiber leads to a spectrometer for analyzing the signal in a manner known as such. Suitable spectrometers are available on the market and are mounted to the base, next to the pivoting mechanism 13.

The optical unit 30 further comprises a camera 71 housed in the upper part 40, a display 75 and associated optical elements, namely a lens package 76 and a dichroic mirror 72. The image shown on the display 75 is imaged by lens package 76 such that it can be perceived by the patient. The image passes the dichroic mirror 72 (shortpass, 700 nm) substantially unaffected, is reflected by the dichroic mirror 53 and enters the eye 99. For focusing purposes, the position of the display 75 may be adjusted along a linear guide 77 by means of an adjusting screw 78 rotating a spindle setting the position of the display 75 with respect to the linear guide 77.

The eye 99 is imaged by the camera 71. For that purpose, the eye is illuminated by LED light sources (red, 750 nm) arranged on a frame of the dichroic mirror 53. The image of the eye 99 is reflected by dichroic mirrors 54, 72 and received by camera 71. A filter may be arranged at the entry of the camera 71 in order to filter out unwanted image components, in particular coming from the display 75 and being reflected by the eye 99. These components are for adjustment, monitoring and tracking purposes.

Figure 6:
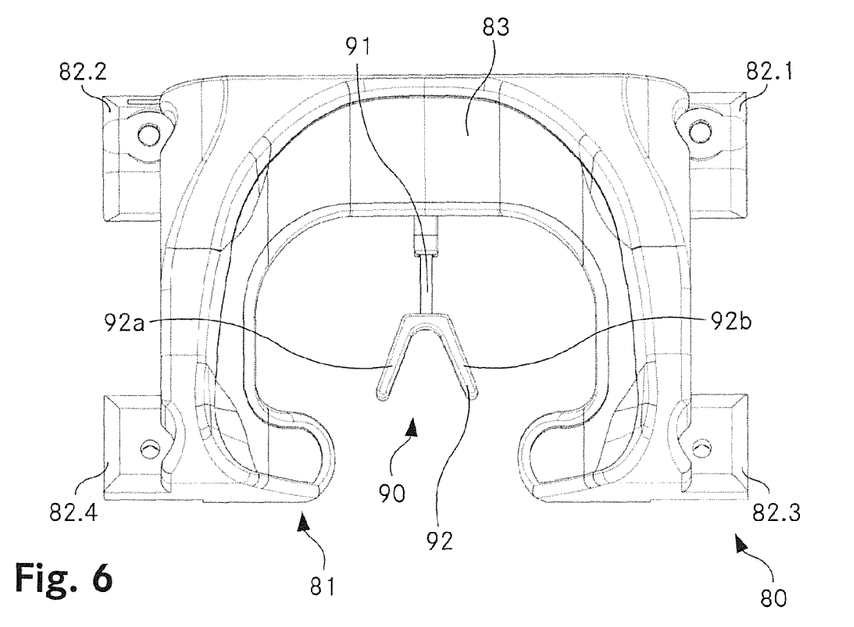
FIG. 6 a top view of the head support of the OCT device.
Figure 7:
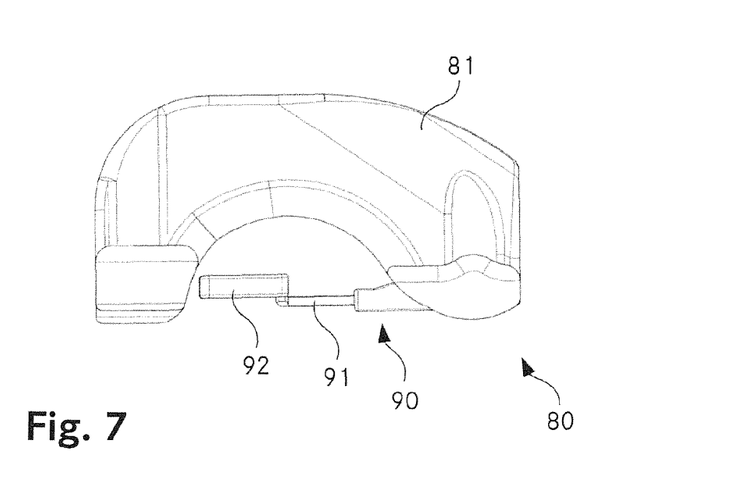
FIG. 7 a side view of the head support.
Figure 8:
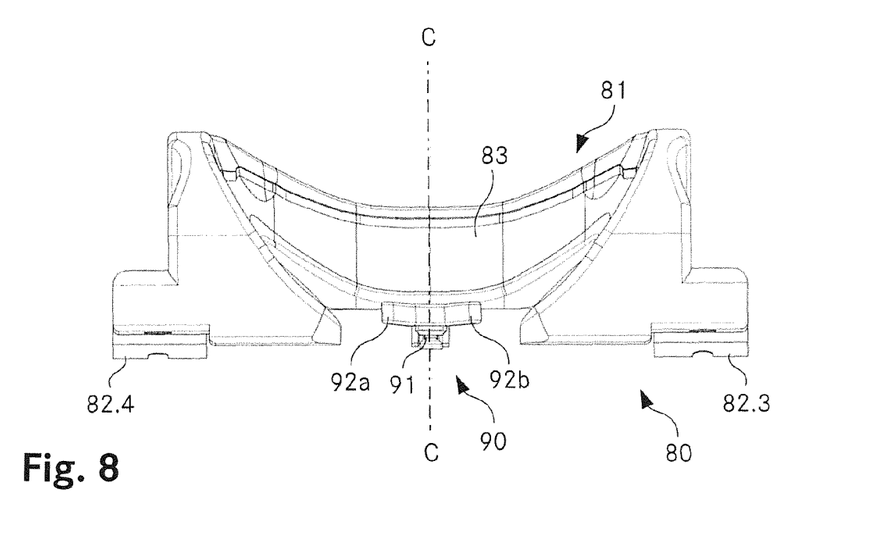
FIG. 8 a back view of the head support.
Figure 9:
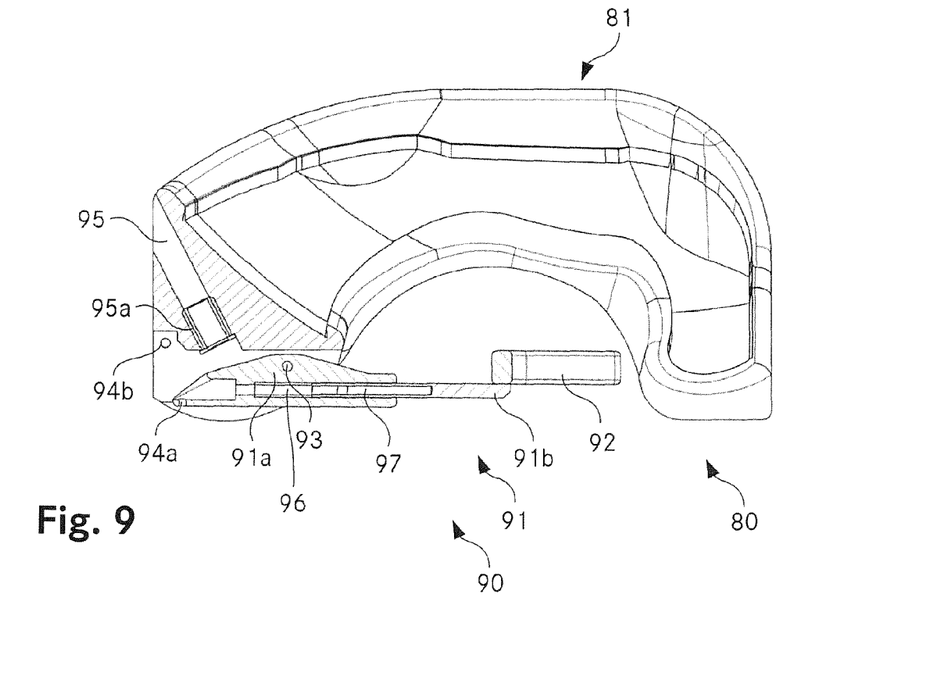
FIG. 9 a cross-sectional view of the head support in a central vertical plane.

The head support 80 of the OCT device is shown in FIGS. 6-9. FIG. 6 shows a top view, FIG. 7 a side view and FIG. 8 a back view. FIG. 9 shows a cross-sectional view of the head support 80 in a central vertical plane.

The head support 80 is constituted of a mask section 81, four attachment flanges 82.1, 82.2, 82.3, 82.4 attached to four corner regions of the mask section 81, and a nose bone clip 90 attached to the mask section 81. The mask section 81 features an accommodation 83 which is shaped according to the typical shape of the region of a human head surrounding the two eyes. In order to accommodate heads of different sizes, a certain number of different sizes of the head support 80 are available. The accommodation 83 provides support for the forehead and the upper parts of the zygomatic bone. For that purpose it comprises roughly a C-shape, extending along an angle of approximately 300°, leaving out a lower sector for accommodating the nose of the patient.

The attachment flanges 82.1 . . . 4 are attached in the outer region of the mask section 81, each flange featuring a fixation opening for attachment of the head support 80 to the housing or a dedicated support structure. Preferably, the mask 80 is attached to the housing or the support structure in a way that allows for adjustment of the mask orientation about a transverse pivot axis.

The nose bone clip 90 is attached to a lower portion of the mask section 81. It comprises a central portion 91 which is attached to the mask section 81 with one end thereof, whereas a bracket piece 92 is attached to the other end of the central portion 91. The central portion 91 is essentially rod-shaped, the bracket piece 92 comprises two legs 92a, 92b connected by a rounded central part and enclosing an angle of about 30°.

The nose bone clip 90 is adjustable. Firstly, the central portion 91 is mounted to the mask section 81 pivotable about a pivot axis 93 perpendicular to the central portion 91 and essentially parallel to the support plane defined by the accommodation 83. A tension spring (not shown) is attached to a rear portion of the central portion 91, namely to an opening 94a, situated behind the pivot axis, as well as to a mounting point of the mask section, namely a bolt accommodated in a further opening 94b of the mask section 81. The pivotal position of the nose bone clip 90 is controlled by the position of a screw (not shown) accommodated in a slanted opening 95 provided with a threaded sleeve 95a. The tip of the screw acts onto the rear portion of the central portion 91 of the nose bone clip 90, counteracting the tension spring and therefore setting the pivotal position of the nose bone clip 90.

Secondly, the extension of the central portion 91 is adjustable. For that purpose, the central portion 91 comprises a base part 91a, including the pivot axis 93, the opening 94a for attaching the tension spring and further a longitudinal opening 96 linearly guiding a front part 91b of the central portion 91. The front part 91b comprises a threaded blind hole 97 leading to the rear surface of the front part 91b. A screw (not shown) is inserted through the longitudinal opening 96 of the base part 91a and interacts with the thread of the blind hole 97. A further tension spring (not shown) is coaxially mounted with the screw and ensures that the screw head contacts a shoulder surrounding the rear end of the longitudinal opening 96. Thereby, the axial position of the front part 91b is unambiguously defined by the position of the screw.

For the examination of both eyes of the patient, the orientation of the optical unit 30 is adjusted using the pivoting mechanism 13, essentially by pivoting the optical unit about the lower pivot axis 14. Adjustments are performed about the other pivoting angle and along the z' direction by the respective mechanisms. Furthermore, the collimation at collimator 45 is adapted to the optical properties of the respective eye.

The invention is not limited to the described example. In particular, the head support may be supplemented by an insert constituting the accommodation for the patient's head. The insert may be made from another material, e.g. an elastic material, and/or it may be manufactured according to the specific geometry of a specific patient's head, thus ensuring precise positioning of the head with respect to the head support. In the latter case, it may be possible to do without the nose bone clip.

The mechanism for moving the optical unit with respect to the base may be embodied differently, in particular, the two pivot axes may be replaced by two linear axes which allow for adjusting the position of the optical unit with respect to the base.

In summary, it is to be noted that the invention creates an OCT imaging device that is inexpensive, compact and easy to use.

The invention claimed is:

1. An optical coherence tomography imaging device for imaging a retina of a human subject, comprising:
   a) a base having a planar contact surface;
   b) an optical unit providing a sample beam to scan the retina of the human subject;
   c) a head support to be contacted by a head portion of the human subject, the head support defining an entrance position of the sample beam entering an eye of the human subject;
   wherein
   d) an angle between the sample beam at the entrance position and the planar contact surface of the base is 50 to 90°.

2. The device as recited in claim 1, wherein the angle is 60 to 90°.

3. The device as recited in claim 2, wherein the angle is 75 to 85°.

4. The device as recited in claim 1, wherein having a tabletop configuration, a distance between the contact surface of the base and the entrance position being 20 to 50 cm.

5. The device as recited in claim 1, wherein the head support comprises a support portion for accommodating an eye portion of the head of the human subject.

6. The device as recited in claim 5, wherein the head support comprises a nose bone clip to contact a nose bone of the human subject.

7. The device as recited in claim 6, wherein the nose bone clip is adjustable in a longitudinal direction.

8. The device as recited in claim 5, wherein an orientation of the nose bone clip about a lateral axis is adjustable.

9. The device as recited in claim 5, wherein the head support comprises an insert that is made to fit a specific anatomy of the head of the human subject.

10. The device as recited in claim 1, wherein the head support is attached to the base in a fixed longitudinal and lateral position, whereas the optical unit is movable with respect to the base in such a way that entrance positions differing in at least a lateral direction are reachable by the sample beam.

11. The device as recited in claim 10, wherein an orientation of the head support about a horizontal lateral axis is adjustable.

12. The device as recited in claim 10, wherein a height of the optical unit with respect to the base is adjustable.

13. The device as recited in claim 1, wherein the optical unit comprises an adjustable collimator lens for adapting the sample beam to an ametropia of the examined eye of the human subject.

14. The device as recited in claim 13, wherein a shape of the collimator lens is adjustable.

15. The device as recited in claim 13, wherein a position of the collimator lens along a beam axis is adjustable.

16. The device as recited in claim 15, wherein the collimator lens is arranged following an output of an optical fiber, whereas the distance between the collimator lens and the output is adjustable.

17. An optical coherence tomography imaging device for imaging a retina of a human subject, comprising:
   a) a base having a planar contact surface;
   b) an optical unit providing a sample beam to scan the retina of the human subject;
   c) a head support to be contacted by a head portion of the human subject, the head support defining an entrance position of the sample beam entering an eye of the human subject;
   wherein
   d) in an operating position of the device the planar contact surface is horizontal and an angle between the sample beam at the entrance position and the planar contact surface of the base is 50 to 90°.

* * * * *